United States Patent
Makikawa et al.

[11] Patent Number: 5,902,214
[45] Date of Patent: May 11, 1999

[54] WALK SIMULATION APPARATUS

[75] Inventors: Masaaki Makikawa, Sakai; Norimasa Tani, Osaka, both of Japan

[73] Assignee: Shiraito Tani, Osaka, Japan

[21] Appl. No.: 08/907,072

[22] Filed: Aug. 6, 1997

[30] Foreign Application Priority Data

Aug. 8, 1996 [JP] Japan .................................. 8-227419

[51] Int. Cl.⁶ .................................................. A63B 69/18
[52] U.S. Cl. .................................. 482/4; 482/52; 482/79; 482/902; 434/247
[58] Field of Search .............................. 482/1–9, 51–53, 482/54, 66, 69–71, 79, 80, 900–902; 434/247, 253, 255; 601/23

[56] References Cited

U.S. PATENT DOCUMENTS

| | | | |
|---|---|---|---|
| 4,986,534 | 1/1991 | Meier et al. | 482/902 |
| 5,308,296 | 5/1994 | Eckstein | 482/5 |
| 5,524,637 | 6/1996 | Erickson | 482/8 |
| 5,562,572 | 10/1996 | Carmein | 482/4 |
| 5,577,981 | 11/1996 | Jarvik | 482/4 |
| 5,583,407 | 12/1996 | Yamaguchi | 482/79 |
| 5,713,794 | 2/1998 | Shimojima et al. | 482/70 |
| 5,792,031 | 8/1998 | Alton | 482/78 |

FOREIGN PATENT DOCUMENTS

07200162  8/1995  Japan .

*Primary Examiner*—Glenn E. Richman
*Attorney, Agent, or Firm*—Armstrong, Westerman, Hattori, McLeland & Naughton

[57] ABSTRACT

A walk simulation apparatus usable for walk training of crippled persons or for a simulator of virtual reality. By the apparatus participants can experience simulations of walking horizontally and on slopes and steps with full reality at the same position. The apparatus is of use also in quantitatively evaluating quality of performances of artificial legs for patients who lost legs. The apparatus comprises a head mounted display showing a participant programmed images in the form of three-dimensional images, a walk surface mechanism having a function of performing simulations of horizontal walk and walk on slopes and steps, a control device, walk plates, and load sensors detecting loads applied on the walk plates individually. The control device has a function of comparing data detected by the load sensors with standard data to analyze a state of walk of the participant.

19 Claims, 8 Drawing Sheets

Fig.10

WALK SIMULATION APPARATUS

BACKGROUND OF THE INVENTION

1. Field of the Invention

The present invention relates to a walk simulation apparatus usable as a trainer for crippled persons to walk or as a virtual reality simulator through which users or participants can experience virtual reality or a virtual world, and more particularly to a walk simulation apparatus which enables users to experience, quasi but with full reality, in the same position walks in various directions or on slopes or steps; is usable by crippled persons or the like to train themselves for walking; and is made use of for quantitatively evaluating achievement in rehabilitation of walk or performance of artificial legs for patients who lost legs.

2. Description of the Prior Art

A walk simulation apparatus hitherto proposed and used for training for walking or as the virtual reality simulator comprises a belt conveyor on which users make a walking motion or exercise in a single direction while being always placed at a fixed or the same position (Japanese Unexamined Patent Application No. 7-200162 (1995)).

In the conventional walk simulation apparatus, the walking motion is performed only in a single direction, and there are not provided experiences of walks on slopes and steps. Hence, the apparatus does not cause users to feel reality as actually walking on an actual walk surface and is not suitable for walk training of the crippled persons or the like. By the same reason the apparatus is hardly of use in quantitatively evaluating extent of achievement in walk rehabilitation of crippled persons or the like and quality of specific performances of artificial legs for patients who lost legs.

SUMMARY OF THE INVENTION

An object of the present invention is to provide a walk simulation apparatus which overcomes the above problems, provides users or participants with walk experiences with full reality as actually walking on an actual walk surface including a horizontal surface, slopes and steps, and is suitable for a walk training.

A further object of the present invention is to provide a walk simulation apparatus which allows users to have walk experiences or a walk training while being placed at a fixed or the same position.

A yet further object of the present invention is to provide a walk simulation apparatus which is of use in quantitatively evaluating extent of achievements in walk rehabilitation, or in quantitatively evaluating or ascertaining the quality of specific performances of artificial legs for patients who lost legs.

Those objects can be accomplished by the present invention described hereunder.

The walk simulation apparatus according to the present invention comprises:

a display showing participants programmed images in the form of three-dimensional images;

a walk surface mechanism which has a function of detecting a foot-bottom position of a participant, and a function of performing a horizontal walk simulation in which left and right walk plates, on which left and right feet of the participant are placed separately, are individually horizontally shifted forward, backward, leftward and rightward, a simulation of walk on slopes in which the left and right walk plates are individually slanted, and a simulation of walk on steps in which the left and right walk plates are individually raised or lowered; and a control device having a function of transmitting the programmed images to the display, and a function of controlling driving of the walk surface mechanism.

According to the invention, the participant can make a walk motion or exercise in various directions at the same position and also have quasi experiences of walk on slopes and steps. Thus, the invention enables the participants to experience walk simulations with full reality and improves the effect of walk training.

A walk simulation apparatus according to the present invention in a modified embodiment includes load sensors for detecting loads applied to each of the left and right walk plates individually, and the control device which has a function of comparing data detected by the load sensors with standard data regarding loads applied to each of the left and right walk plates to make analysis of a state of walk of the participant.

According to the invention, the state of walk of the participant can be evaluated by comparing the walk state with the standard walk state. Hence, the invention is applicable to quantitatively evaluating extent of achievement of walk rehabilitation of crippled persons, etc., and is also of use in quantitatively evaluating performances of any artificial legs employed by participants.

The walk surface mechanism may preferably comprise the left and right walk plates and a walk-plate drive connected to and supporting the walk plates, and preferably the walk-plate drive may be disposed in a pit formed on a floor of a play room.

According to the invention, participants may be allowed to perform exercises such as walk or running correspondingly to the three-dimensional images and at the same position in a narrow space.

The walk plates may preferably have a foot-position regulating frame for regulating the participant's feet in a predetermined position. And the walk surface mechanism may be provided with a foot bottom-position detecting means which is for detecting positions of feet bottoms of the participants and may preferably comprise a signal transmission member provided on each of left and right shoes to be put on by participants and a sensor which is mounted on each of the left and right walk plates to receive signals from the signal transmission member. By this feature, the foot bottom-position detecting means is simple in structure.

A walk simulation apparatus according to the present invention in a further modified embodiment comprises the walk plate drive which includes a horizontally-driving means for shifting each of the left and right walk plates individually and horizontally forward, backward, leftward and rightward, a slantwise-driving means for slanting each of the left and right walk plates individually and slantwise forward, backward, leftward and rightward, and a raising and lowering means for raising and lowering each of the left and right walk plates individually. In this case, it is preferable that the horizontally-driving means has an initial state setting function to shift the walk plates to allow the feet bottoms of participants to be placed in a foot-supporting position and direction on the walk plates, and a forcibly exercising function to pull back the walk plate, on which the participant has trodden at his or her foot bottom, toward the participant's trunk, correspondingly to kinds of exercises such as walk or running, thereby keeping the participant's trunk in a fixed or constant position.

The raising and lowering means for the walk plates may employ a raising and lowering cylinder which changes the height of the left and right walk plates individually. Further, the horizontally-driving means may comprise a rotation cylinder fit to a piston rod of the raising and lowering means, a swinging cylinder for swinging the raising and lowering means forward and backward, and a swinging cylinder for swinging the raising and lowering means leftward and rightward. Furthermore, it is preferable that the raising and lowering means has at its lower end a fulcrum around which it swings, and a radius of swinging extending from the fulcrum to the walk plate at the upper end of the piston rod is long enough to cause the participants to feel in their bodies the forward, backward, leftward and rightward swinging of the raising and lowering means as a horizontal shift.

The slantwise-driving means may comprise a longitudinally swinging cylinder and a widthwise swinging cylinder for swinging the walk plates in their longitudinal direction and widthwise respectively.

A walk simulation apparatus according to the present invention in yet another modified embodiment comprises the walk surface mechanism which includes a walk base plate freely tilted, the left and right walk plates held by the walk base plate as being capable of being freely horizontally shiftable and rotatable, and a walk-plate slantwise-driving means which supports one end of the walk base plate. In this case, it is preferable that the walk surface mechanism includes a walk base plate freely tilted, the left and right walk plates held by the walk base plate as being capable of being freely horizontally shiftable and rotatable, and a walk-plate slantwise-driving means which supports one end of the walk base plate.

A walk simulation apparatus according to the present invention in a further modified embodiment comprises the walk surface mechanism which includes the left and right walk plates, a walk-plate support base supporting each walk plate, and a walk-plate horizontally-driving means for horizontally shifting the walk plate support bases, the horizontally-driving means including a bendable linkage mechanism and a rotation cylinder disposed at a joint in the linkage mechanism.

Other various and characteristic features and functions of the present invention will be further made apparent in the specific examples described hereunder.

DETAILED DESCRIPTION OF THE PREFERRED EMBODIMENT

Next, an example of the present invention will be detailed with referring to the accompanied drawings FIGS. 1 to 5.

Figure 1:
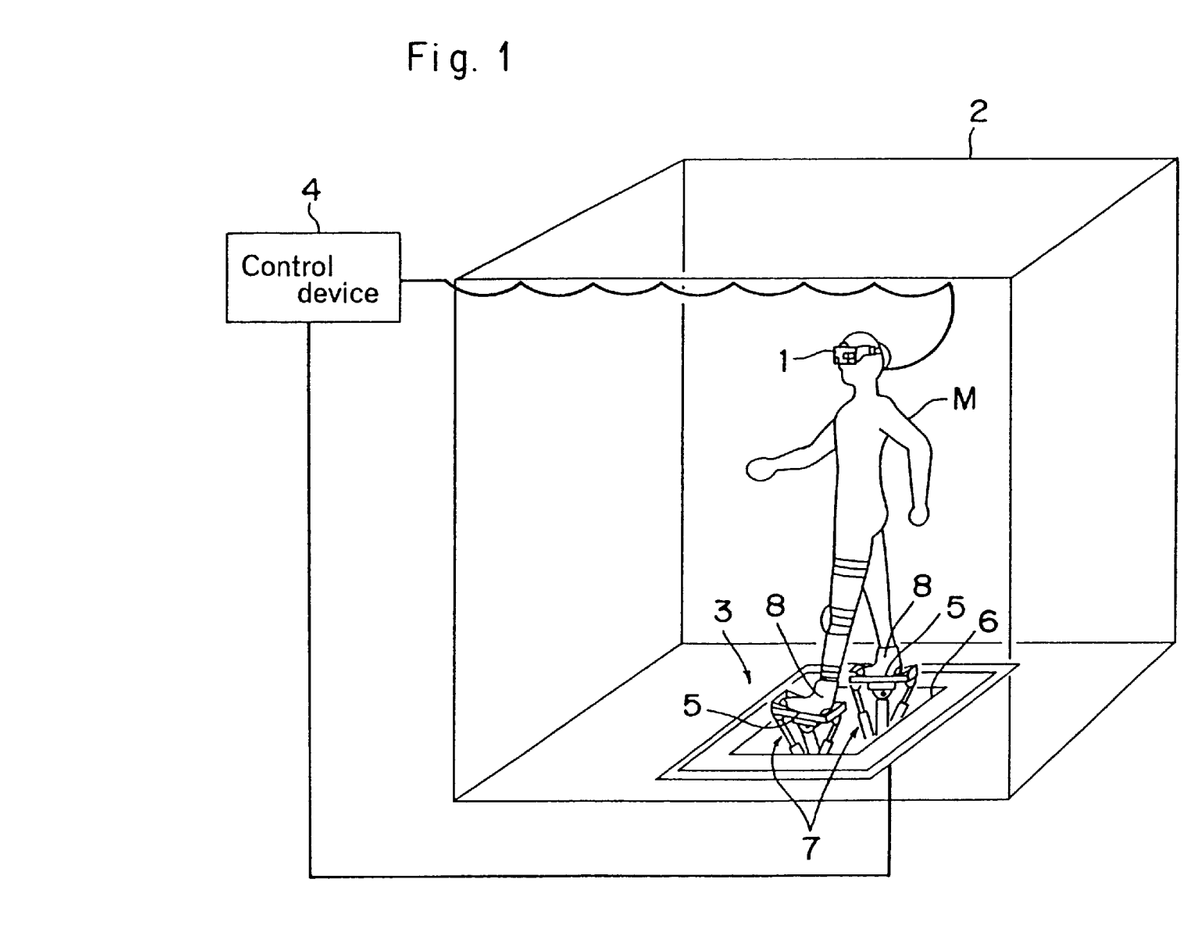
FIG. 1 is a schematic explanatory view showing a structure of a walk simulation apparatus in an example according to the present invention.

FIG. 1 schematically shows a structure of a walk simulation apparatus according to the present invention in this example. The walk simulation apparatus is in the form of a model used in a walk training for crippled persons such as patients or cases who lost legs partially or entirely or are of hemiplegia due to aftereffect of cerebrovascular disease. The walk simulation apparatus has a head-mounted display 1 (called hereunder "HMD"), which shows a participant M previously programmed images, a walk surface mechanism 3 arranged on a floor in a play room 2, and a control device 4 including CPU. The HMD 1 is put on by the participant M on the head and has a function of showing the participant M any images previously programmed in the control device 4, for example, images formed by computer graphics and shown in the form of three-dimensional images. The control device 4 has functions of controlling driving of the walk surface mechanism 3, and of transmitting the programmed images to the HMD 1.

The walk surface mechanism 3 includes a pair of walk or foot plates 5 each supporting the participant's left and right feet, respectively. The walk plates 5 are each connected to and separately supported by each of a pair of walk-plate drive 7 which stand inside and project from a pit 6 formed on a floor of a play room 2 and are adapted to drive the walk plates 5.

Figure 4:
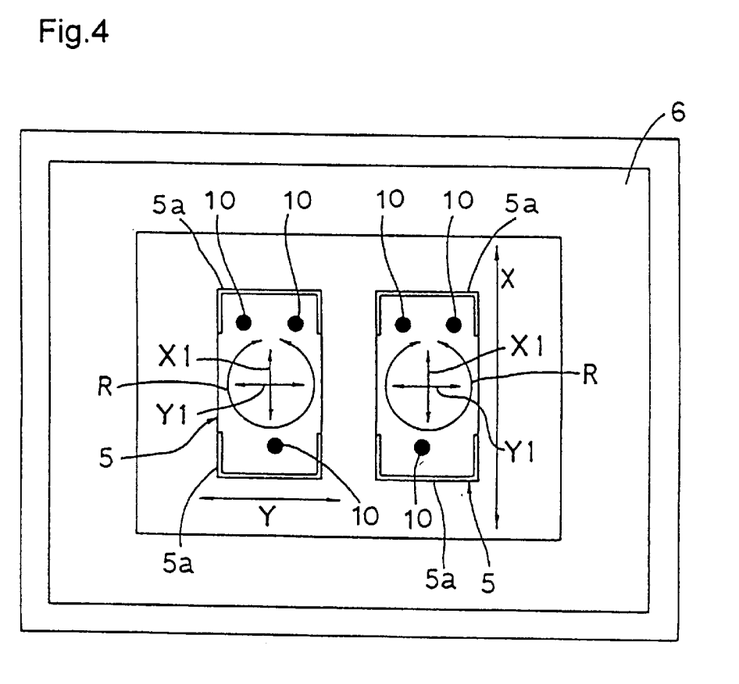
FIG. 4 is a plan view of the walk surface mechanism.

The walk plate 5 has on the edge a foot-position regulating frame 5a for regulating the participant's foot in a predetermined foot-position. The participant M puts on shoes 8 and places his or her feet on the walk plates 5. The shoes 8 mount at predetermined points a plurality (three in this example) of signal transmission member 9 which transmits particular standard signals, which are preferably ultrasonic waves or may adopt other signal mediums such as line of magnetic force, infrared rays, etc. FIG. 4 shows a plurality (three in this example) of sensors 10 set on the walk plates 5 at the foot-supporting position, i.e., at specific points corresponding to the signal transmission members 9 provided on the shoes 8 which are placed on the walk plates 5 at the foot-supporting position. Each sensor 10 corresponds individually to a specific one of the plurality of signal transmission members 9, and has such function that when the shoe 8 is moved away from the walk plate 5, each sensor 10 individually receives the standard signal transmitted from the specific or corresponding signal transmission member 9 to thereby detect specific positions of the foot bottom of the participant which has been moved away from the walk plate 5. Accordingly, the signal transmission members 9 at the shoes 8 and the sensors 10 on the walk plates 5 constitute a foot bottom-position detecting means 11.

The walk-plate drive 7 has a horizontally-driving means 13, a slantwise-driving means 14 and a raising and lowering means 15.

The horizontally-driving means 13 has functions, such as an initial-state setting function that shifts the walk plates 5 to allow the foot bottom of the participant M to be placed and set in a predetermined foot-supporting position and direction on the walk plates 5, and a forcibly exercising function that does, correspondingly to kinds of exercises such as walking and running, pull back the walk plate 5 (on which one of the feet of the participant, i.e., a foot bottom, has been placed or has trodden) toward the trunk of the participant M to thereby keep the participant's trunk in a constant or fixed position. The slantwise-driving means 14 has a slanting function of slanting the walk plates 5 for a simulation of walking on slopes. And the raising and lowering means 15 has a raising and lowering function for moving upwards and downwards the left and right walk plates 5 separately or individually for a simulation of walking on steps.

Figure 5A:
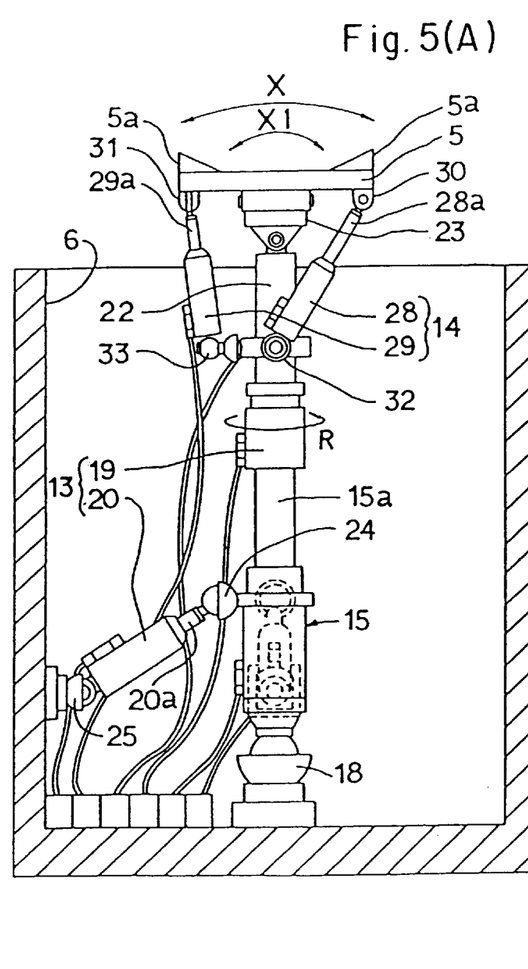
FIG. 5(A) is a sectional side view of the walk surface mechanism, and FIG. 5(B) a sectional rear view of the same.
Figure 5B:
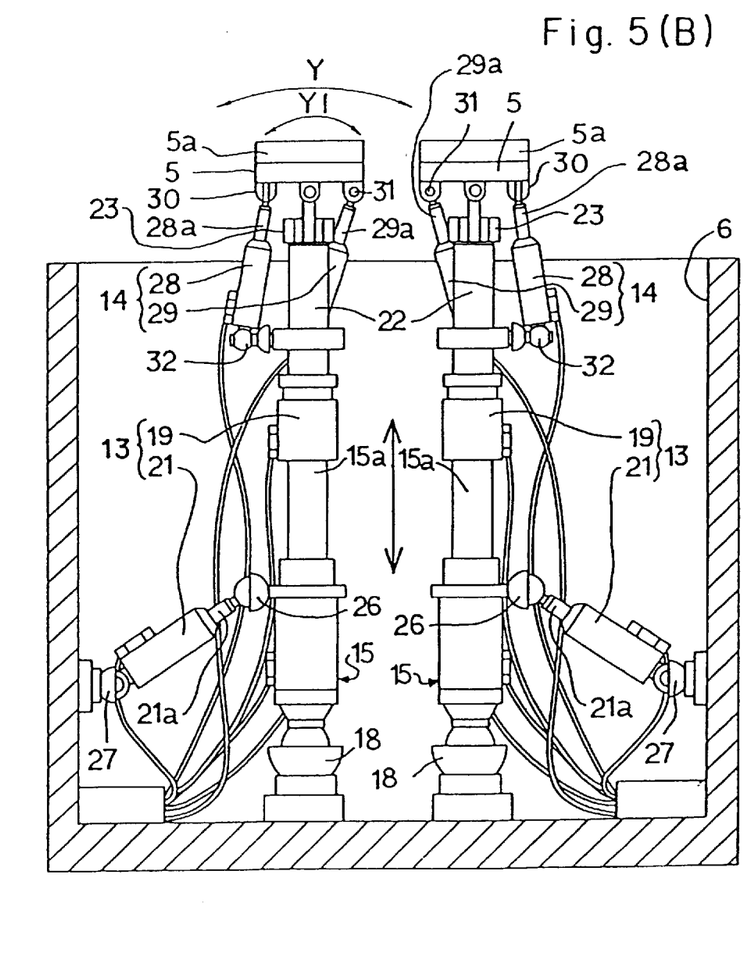

As shown in FIG. 5, the raising and lowering means 15 comprises a raising and lowering cylinder which stands on the bottom of the pit 6 through a universal joint 18 and is driven to change heights of the walk plates 5 individually for the simulation of walking on steps.

The horizontally-driving means 13 does, as seen in FIG. 5, comprise a rotation cylinder 19 fit to a piston rod 15a of the raising and lowering means 15; a forward and backward swinging cylinder 20 for swinging the raising and lowering means 15 forward and backward (in the direction designated by X) as shown in FIG. 5(A); and a leftward and rightward swinging cylinder 21 for swinging the raising and lowering means 15 leftward and rightward (in the direction Y). A rotation rod 22 which is driven and rotated by the rotation cylinder 19 is connected to a central part of the bottom of the walk plate 5 through a universal joint 23. A piston rod 20a of the forward and backward swinging cylinder 20 is connected to the raising and lowering means 15 through a universal joint 24, and a rear end of the cylinder 20 is supported on a wall surface of the pit 6 through a universal joint 25. Moreover, the leftward and rightward swinging cylinder 21 is connected at its piston rod 21a to the raising and lowering means 15 through a universal joint 26 and is connected at its rear end on the wall surface of the pit 6 through a universal joint 27. By this feature, the walk plate 5 is swingable forward and backward and leftward and rightward and also rotatable around the rotation rod 22 (in the direction R in FIG. 4). In this case, a radius of swinging extending from the universal joint 18 (serving as a fulcrum for the forward, backward, leftward and rightward swinging) to the walk plate 5 is fully long. Thus, the forward, backward, leftward and rightward swinging may be regarded to be substantially the same, in the participants' feelings in their bodies, as the horizontal shift in the same directions.

As shown in FIG. 5, the slantwise-driving means 14 comprises a longitudinally-swinging cylinder 28 and a widthwise-swinging cylinder 29, which are each connected between the rotation rod 22 and the walk plate 5 to swing the walk plate 5 in its longitudinal direction X1 and widthwise direction Y1, respectively. The swinging cylinders 28, 29 are connected at their piston rods 28a, 29a to specific points on the bottom surface of the walk plate 5 through universal joints 30 and 31, respectively, and are also connected at their rear ends to the rotation rod 22 through universal joints 32, 33. By this feature, the left and right walk plates 5 are separately capable of being slanted in the forward and backward direction X1 and in the leftward and rightward direction Y1, thereby providing the simulation of walking on slopes.

Figure 2:
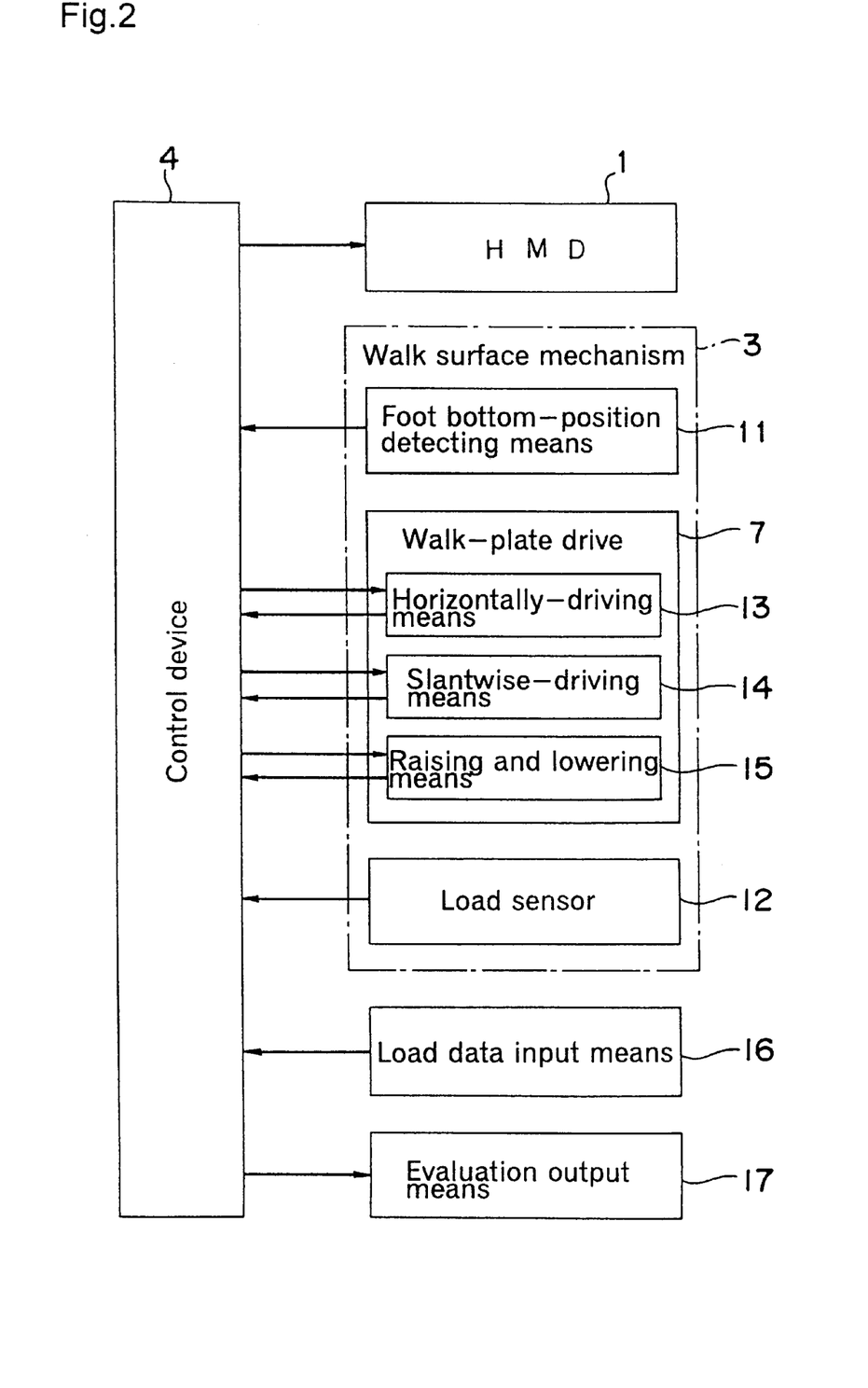
FIG. 2 is a block diagram showing a system of control for the walk simulation apparatus.
Figure 3:
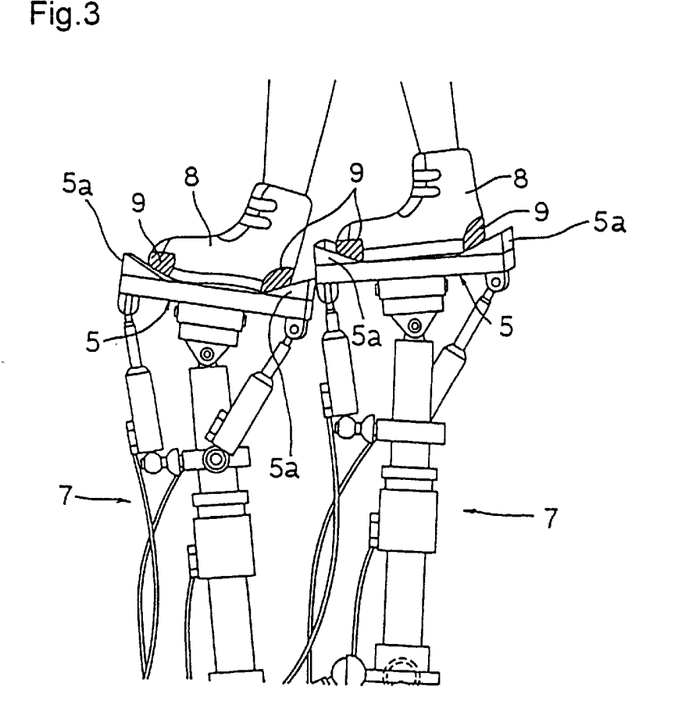
FIG. 3 is an explanatory view of a walk surface mechanism, being in use, provided in the walk simulation apparatus.

The left and right walk plates 5 have load sensors 12 implanted at plural points on the foot-supporting positions, which load sensors each detect loads applied on each point when the participant M places the foot on the walk plate 5 (See FIG. 2). Data of loads detected by the load sensors 12 are input to the control device 4. Furthermore, connected to the control device 4 as shown in FIG. 2 are a load data input means 16 which inputs standard load data including loads applied on the left and right feet at their treading points in healthy persons' walking and other factors, and an evaluation output means 17 including a printer, a display, etc., for outputting evaluation results of walk exercises of the participant M. The control device 4 makes comparison and analysis of the load data detected by the load sensors 12 and the standard load data previously given in the control device 4 by the load data input means 16 and makes evaluation, on the basis of the analysis results, of the walk exercise of the participant M.

According to the walk simulation apparatus referred to above, images previously programmed are transmitted from the control device 4 to the HMD 1 mounted on the head of the participant M, so that the participant can watch and listen to the three-dimensional images. When the participant M tries to make motions or exercise of walking or running correspondingly to the three-dimensional images that the participant is watching and listening to, and the bottom of the left or right foot is brought into contact with the corresponding predetermined position on the walk plate 5, the horizontally-driving means 13 of the walk surface mechanism 3 functions to forcibly pull back the walk plate 5 (on which the participant has trodden or the foot bottom has been contacted) toward the trunk of the participant M, whereby the trunk can be kept in a constant or fixed position. The operation is carried out repeatedly and alternately for the left and right feet to enable the participant M to perform exercising of walk or running on the same position in a narrow space correspondingly to the three-dimensional images. Furthermore, the slantwise-driving means 14 of the walk surface mechanism 3 causes the walk plate 5 to be slanted correspondingly to the three-dimensional images to provide the participant M with a quasi experience of walking on slopes. Moreover, the raising and lowering means 15 changes separately the left and right walk plates 5 in height correspondingly to the three-dimensional images, thereby providing a quasi experience of walking on steps. Operations of those are mixed synergistically or cooperatively to achieve a realistic walk simulation or experience.

In case that the walk simulation apparatus is used for a walk training of crippled persons, for example, of hemiplegia due to aftereffect of cerebrovascular disease, the control device 4 makes comparison and analysis of the standard load data of healthy persons' walk previously given by the load data input means 16 and load data detected by the load sensors 12 on the walk plates 5 to make evaluation of the state of walking. And results of the evaluation is output by the evaluation output means 17. By this, extent of achievement of walk rehabilitation of the crippled persons can be evaluated quantitatively. Furthermore, the walk simulation apparatus may be used by people mounting artificial legs. In such case, the evaluation results output from the evaluation output means 17 is made use of for evaluating performances of the artificial legs, enabling the artificial legs to be improved more effectively.

Figure 6:
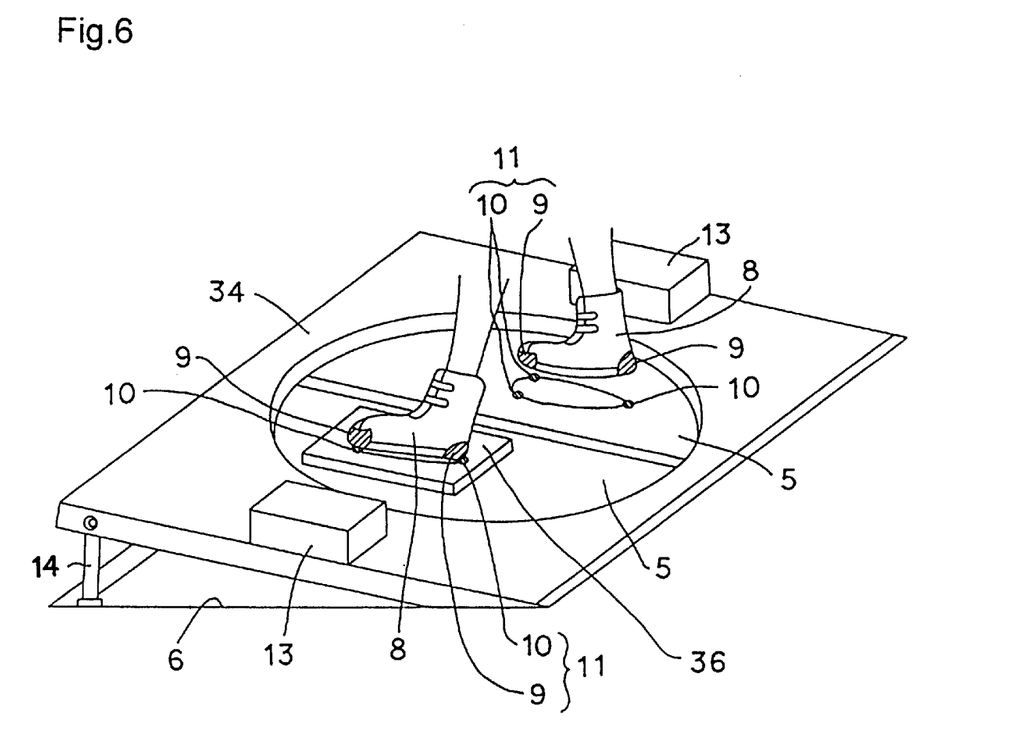
FIG. 6 is an explanatory perspective view of a walk surface mechanism in a further example, being in use, in the walk simulation apparatus.
Figure 7A:
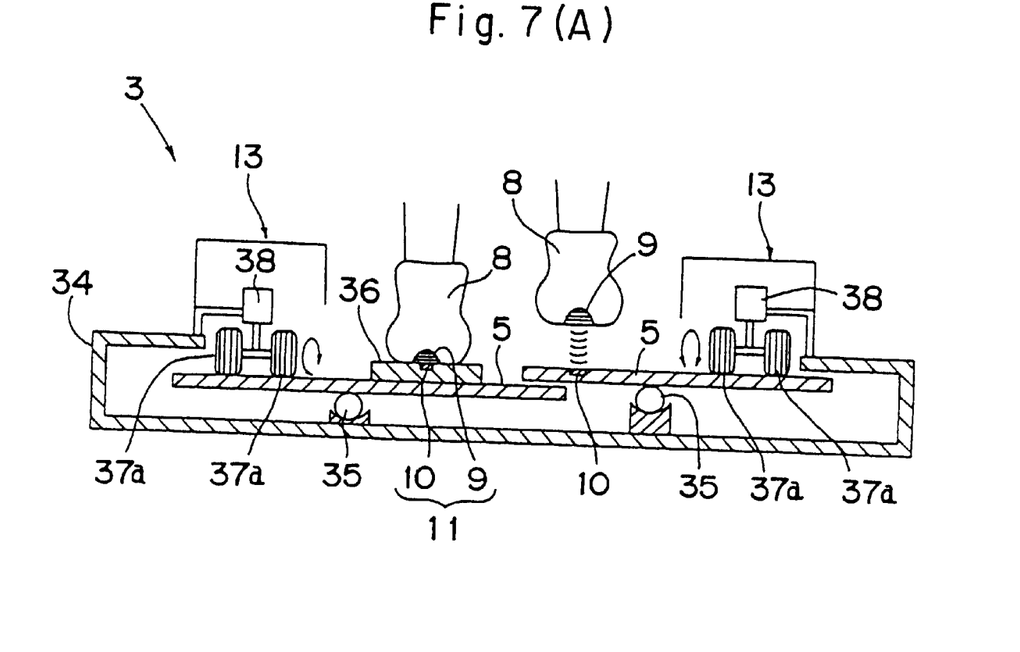
FIG. 7(A) is a longitudinally sectional view of the walk surface mechanism in FIG. 6, and FIG. 7(B) a plan view showing a walk-plate horizontally-driving means in the same walk surface mechanism.
Figure 7B:
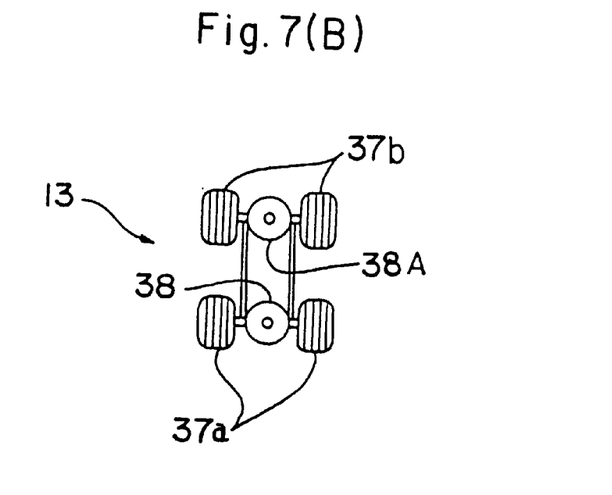

FIGS. 6 and 7 illustrate another example of the walk surface mechanism 3.

The walk surface mechanism 3 in this example has a walk base plate 34 which is laid on the floor of the play room 2 as being freely tilted and is provided with a pair of walk plates 5 as being freely rotatable and shiftable forward, backward, leftward and rightward. The walk base plate 34 is supported at one end by a slantwise-driving means 14 including a cylinder and other parts. The slantwise-driving means 14 is actuated to slant the base plate 34 together with the walk plates 5, thereby providing simulation of walking on slopes.

The left and right walk plates 5 are shifted forward, backward, leftward and rightward and rotated by means of a horizontally-driving means 13 arranged on the walk base plate 34 correspondingly to each walk plate 5.

FIG. 7(A), the longitudinally sectional view, shows the left and right walk plates 5 supported by free balls 35 disposed on the bottom of the base plate 34 as being freely rotatable. The walk plates 5 are different in height to each other by the extent of their thickness to thereby be prevented from interfering with each other. The low walk plate 5 is provided at its foot-supporting position with a treading plate 36 for height adjustment to offset the above height difference of the walk plates.

The horizontally-driving means 13 for the walk plates 5 does, as seen in FIGS. 7(A) and 7(B), comprise a pair of rollers 37a for forward and backward movement and a pair of rollers 37b for rotation, the rollers 37a and 37b being in contact with the corresponding walk plates 5, and motors 38 and 38A driving to rotate the forward/backward movement rollers 37a and the rotation rollers 37b, respectively. Rotation of the left or right walk plate 5 is carried out by driving to rotate the left and right rotation rollers 37b at different rotational speed or number of revolutions per minute.

Figure 8A:
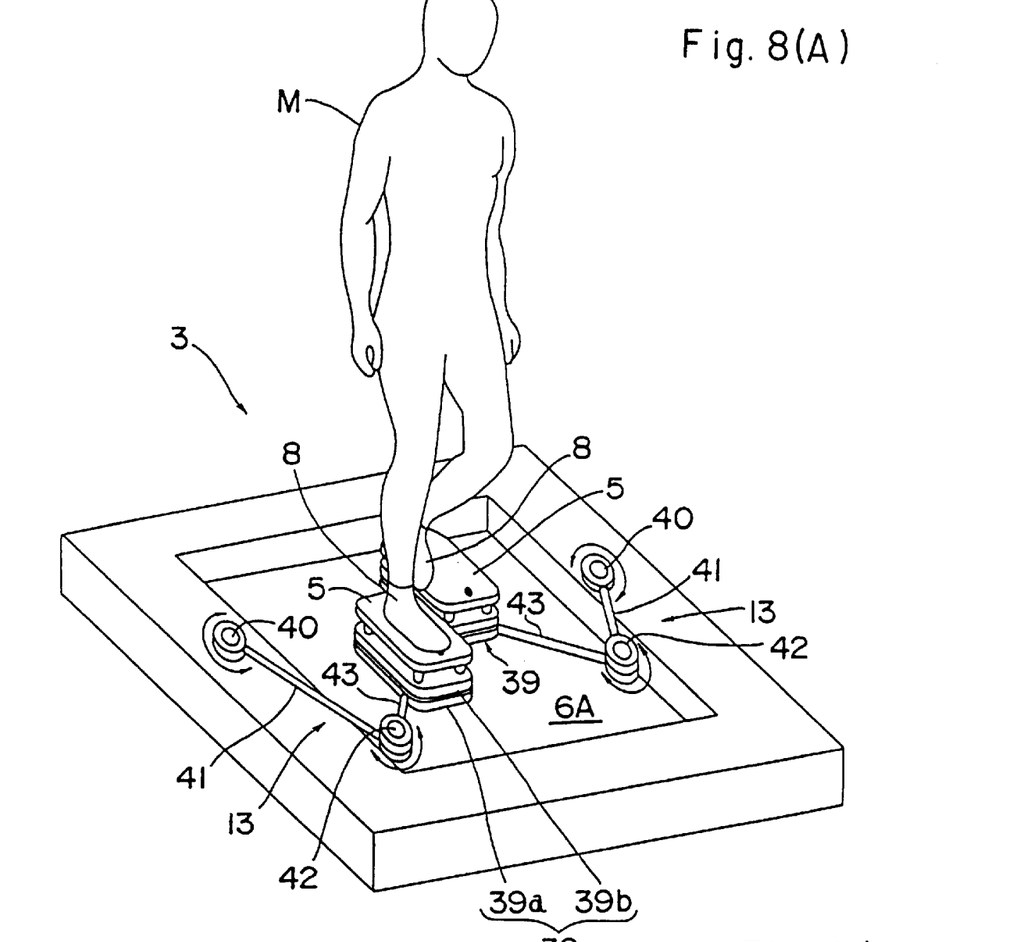
FIG. 8(A) is an explanatory perspective view of a walk surface mechanism in a yet further example, being in use, in the walk simulation apparatus, and FIG. 8(B) a plan view of a principal portion of the same walk surface mechanism.
Figure 8B:
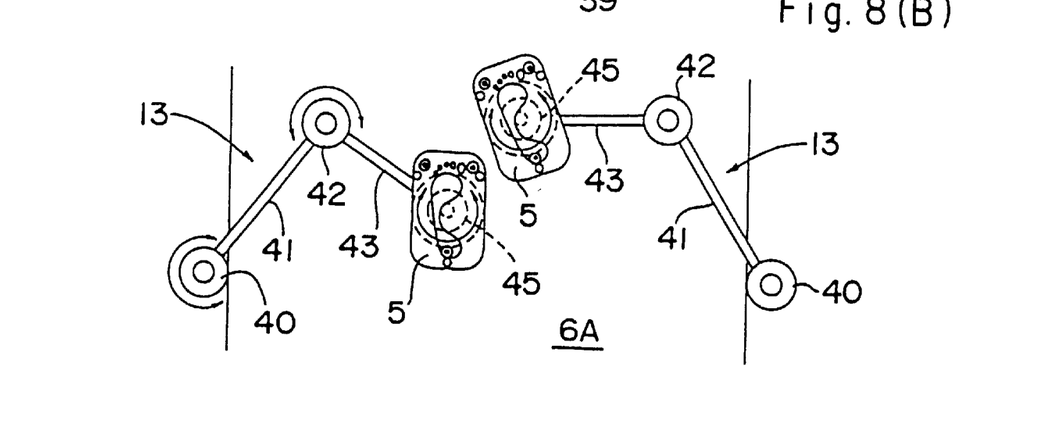
Figure 9:
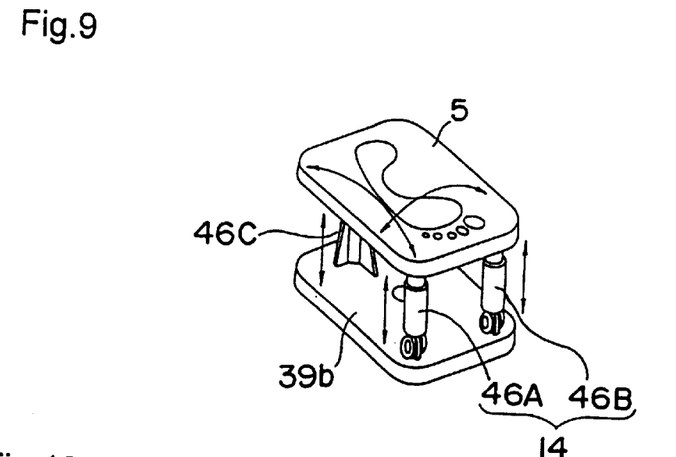
FIG. 9 is a perspective view of a walk-plate support base in the same walk surface mechanism.
Figure 10:
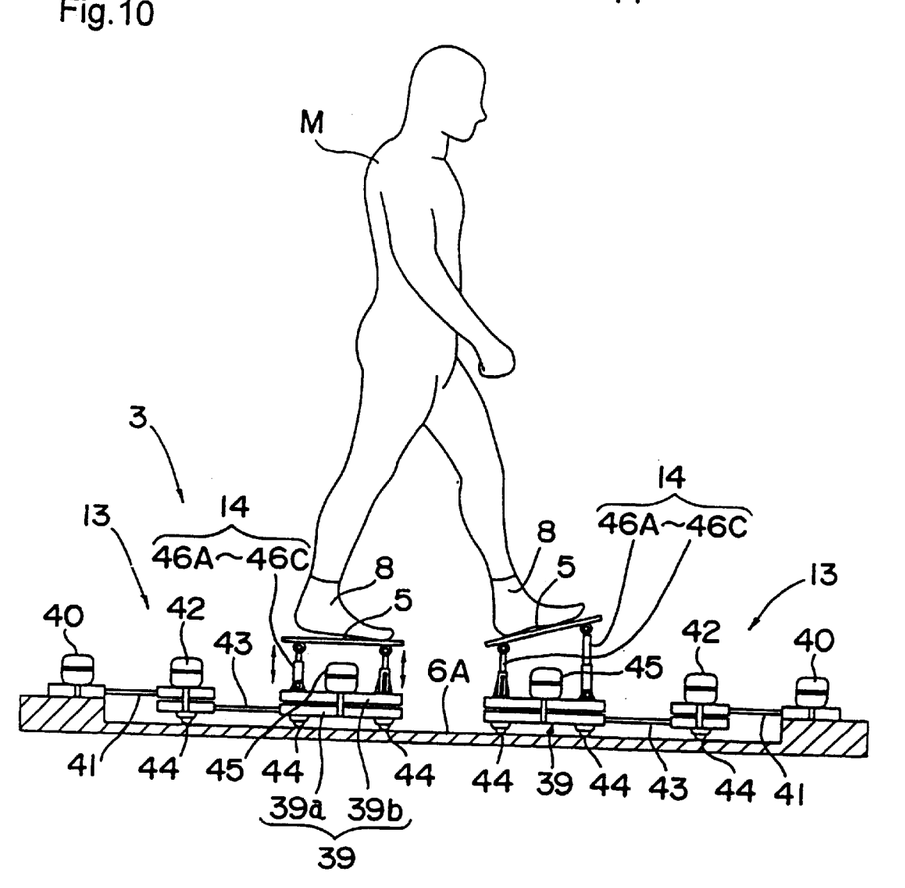
FIG. 10 is a longitudinally sectional view showing the same walk surface mechanism.

FIGS. 8 to 10 show yet another example of the walk surface mechanism 3.

In this example, the left and right walk plates 5 are arranged in a shallow pit 6A formed on the floor and are supported by support bases 39. The left and right support bases 39 are movable horizontally by use of a walk-plate horizontally-driving means 13 including a linkage mechanism. The linkage mechanism forming the horizontally-driving means 13 comprises a first rotation cylinder 40 on the mouth edge of the pit 6A, a first arm 41 swingable by the rotation cylinder 40, a second rotation cylinder 42 at a remote end of the arm 41 and a second arm 43 connecting the rotation cylinder 42 with the walk-plate support base 39. By the horizontally-driving means 13, the rotation cylinders 40 and 42 are controlled to rotate so that the arms 41 and 43 are swung to horizontally shift the walk-plate supporting bases 39 in the pit 6A. Free rollers 44 are provided on the bottom surfaces of the joint or connecting parts of the arms 41, 43 and at the bottoms of the support bases 39 for making smooth the horizontal movement of the walk plates.

The support base 39 includes a lower base 39a directly connected to the second arm 43 and an upper base 39b mounted on the lower base 39a in a manner of being freely rotatable. The upper base 39b is driven, by a third rotation cylinder 45 mounted thereon, to rotate with respect to the lower base 39a. The walk plate 5 is supported on the upper base 39b by three raising-lowering cylinders 46A, 46B, 46C. Hence, the walk plate 5 may be slanted by adjusting the height of the two fore cylinders 46A and 46B and the hind one 46C. That is, the raising-lowering cylinders 46A, 46B, 46C form a slantwise-driving means 14 for the walk plates. Furthermore, the two fore cylinders 46A and 46B may be caused to differ in height from each other to slant the walk plates 5 widthwise. And all the raising-lowering cylinders 46A, 46B, 46C may be raised or lowered by a predetermined level at a time to make simulation of walking on steps. Moreover, the rotation cylinder 45 on the upper base 39b is driven to rotate, so that the walk plate 5 is rotated on the support base 39. Other features in this example are the same as those in the foregoing examples of the walk surface mechanism 3.

What is claimed is:

1. A walk simulation apparatus comprising:
    a display showing participants programmed images in the form of three-dimensional images;
    a walk surface device for detecting a foot-bottom position of a participant, and for performing a horizontal walk simulation in which left and right walk plates, on which left and right feet of the participant are respectively placed, are shifted individually and horizontally forward, backward, leftward and rightward, wherein the walk surface device performs a simulation of walk on slopes in which the left and right walk plates are individually slanted, and wherein the walk surface device further performs a simulation of walk on steps in which the left and right walk plates are individually raised or lowered; and
    a control device for transmitting the programmed images to the display, and for controlling driving of the walk surface device.

2. A walk simulation apparatus as set forth in claim 1, further comprising load sensors for separately detecting loads applied to each of the left and right walk plates individually, wherein the control device compares data detected by the load sensors with standard data regarding loads applied to each of the left and right walk plates to analyze a state of walk of the participant.

3. A walk simulation apparatus as set forth in claim 1, wherein the display is a head mounted display mounted on the head of the participant.

4. A walk simulation apparatus as set forth in claim 1, wherein the walk surface device includes the left and right walk plates and a walk-plate drive connected to and supporting the walk plates.

5. A walk simulation apparatus as set forth in claim 4, wherein the walk-plate drive is disposed in a pit formed on a floor of a play room.

6. A walk simulation apparatus as set forth in claim 4, wherein the walk plate has a foot-position regulating frame for regulating the participant's foot in a predetermined position.

7. A walk simulation apparatus as set forth in claim 1, wherein the walk surface device includes a foot bottom-position detecting means for detecting positions of feet bottoms of the participant and further includes a signal transmission member provided on each of left and right shoes to be put on by participants and a sensor which is mounted on each of the left and right walk plates to receive signals from the signal transmission member.

8. A walk simulation apparatus as set forth in claim 7, wherein the signal transmission members are on a plurality of points on each of the left and right walk plates.

9. A walk simulation apparatus as set forth in claim 7, wherein the signal transmission member transmits an ultrasonic signal.

10. A walk simulation apparatus as set forth in claim 4, wherein the walk plate drive includes a horizontally-driving means for shifting each of the left and right walk plates individually and horizontally forward, backward, leftward and rightward; a slantwise-driving means for slanting each of the left and right walk plates individually and slantwise forward, backward, leftward and rightward; and a raising and lowering means for raising and lowering each of the left and right walk plates individually.

11. A walk simulation apparatus as set forth in claim 10, wherein the horizontally-driving means has an initial state setting function to shift the walk plates to allow the feet bottoms of participants to be placed in a foot-supporting position and direction on the walk plates, and a forcibly exercising function to pull back the walk plate, on which the participant has trodden at their foot bottom, toward the participant's trunk correspondingly to kinds of exercises, thereby keeping the participant's trunk in a fixed or constant position.

12. A walk simulation apparatus as set forth in claim 10, wherein the raising and lowering means for the walk plates comprises a raising and lowering cylinder which changes the height of the left and right walk plates individually.

13. A walk simulation apparatus as set forth in claim 11, wherein the horizontally-driving means comprises a rotation cylinder fit to a piston rod of the raising and lowering means, a swinging cylinder for swinging the raising and lowering means forward and backward, and a swinging cylinder for swinging the raising and lowering means leftward and rightward.

14. A walk simulation apparatus as set forth in claim 10, wherein the raising and lowering means has, at a lower end thereof a fulcrum around which the raising and lowering means swings.

15. A walk simulation apparatus as set forth in claim 10, wherein the slantwise-driving means comprises a longitudinally swinging cylinder and a widthwise swinging cylinder for swinging the walk plates in their longitudinal direction and widthwise respectively.

16. A walk simulation apparatus as set forth in claim 1, wherein the walk surface device comprises a walk base plate freely tilted, the left and right walk plates held by the walk base plate as being capable of being freely horizontally shiftable and rotatable, and a walk-plate slantwise-driving means for supporting one end of the walk base plate.

17. A walk simulation apparatus as set forth in claim 2, wherein the walk surface device comprises a walk base plate freely tilted, the left and right walk plates being freely horizontally shiftable and rotatable, and a walk-plate slantwise-driving means for supporting one end of the walk base plate.

18. A walk simulation apparatus as set forth in claim 1, wherein the walk surface device comprises the left and right walk plates, a walk-plate support base supporting each walk plate, and a walk-plate horizontally-driving means for horizontally shifting the walk-plate support bases, the horizontally-driving means including a bendable linkage device and a rotation cylinder disposed at a joint in the linkage device.

19. A walk simulation apparatus as set forth in claim 2, wherein the walk surface device comprises the left and right walk plates, a walk-plate support base supporting each walk plate, and a walk-plate horizontally-driving means for horizontally shifting the walk-plate support bases, the horizontally-driving means including a bendable linkage device and a rotation cylinder disposed at a joint in the linkage device.

* * * * *